United States Patent
Sisler et al.

(10) Patent No.: US 10,281,310 B2
(45) Date of Patent: May 7, 2019

(54) WEIGHT-BASED PHASE COMPOSITION RATIO DETERMINATION

(71) Applicants: John R. Sisler, Scotts Valey, CA (US); Kenneth D. Boetzer, Scotts Valley, CA (US); Sadiq Jafar Mohammed Zarrouk, Auckland (NZ)

(72) Inventors: John R. Sisler, Scotts Valey, CA (US); Kenneth D. Boetzer, Scotts Valley, CA (US); Sadiq Jafar Mohammed Zarrouk, Auckland (NZ)

(73) Assignees: AUCKLAND UNISERVICES LIMITED, Auckland (NZ); STEAMFIELD SENSORS, INC., Scotts Valley, CA (US)

( * ) Notice: Subject to any disclaimer, the term of this patent is extended or adjusted under 35 U.S.C. 154(b) by 198 days.

(21) Appl. No.: 15/464,168

(22) Filed: Mar. 20, 2017

(65) Prior Publication Data
US 2017/0322063 A1 Nov. 9, 2017

Related U.S. Application Data

(63) Continuation of application No. PCT/US2015/050808, filed on Sep. 17, 2015.
(Continued)

(51) Int. Cl.
*G01F 1/74* (2006.01)
*G01G 1/00* (2006.01)
(Continued)

(52) U.S. Cl.
CPC ............ *G01F 1/74* (2013.01); *E21B 47/0003* (2013.01); *E21B 47/10* (2013.01); *F24T 10/20* (2018.05);
(Continued)

(58) Field of Classification Search
None
See application file for complete search history.

(56) References Cited

U.S. PATENT DOCUMENTS 6,318,156 B1   11/2001   Dutton et al.
2006/0247869 A1   11/2006   Lucero
(Continued)

FOREIGN PATENT DOCUMENTS

CN   103226641 A   7/2013

OTHER PUBLICATIONS

International Search Report and Written Opinion PCT/US15/50808 dated Dec. 18, 2015, pp. 1-8.

*Primary Examiner* — Harshad R Patel
(74) *Attorney, Agent, or Firm* — Perkins Coie LLP (57) ABSTRACT

Several embodiments include a method of computing a phase composition ratio of a two-phase mixture in a pipe. For example, the phase composition ratio is a void fraction or a dryness fraction. The two-phase mixture can have one or more material substances that do not travel as a whole (e.g., at least two of solid phase, liquid phase, and gaseous phase or two liquid materials of different densities that do not mix). A load cell can measure, continuously, weight of the pipe and content of the pipe. Then, a computing system or a circuit can compute, continuously, a moving average of the continuously measured weight. The computing system or the circuit can compute a change in the phase composition ratio of the two-phase mixture based on the computed moving average.

33 Claims, 7 Drawing Sheets

Related U.S. Application Data

(60) Provisional application No. 62/054,782, filed on Sep. 24, 2014.

(51) Int. Cl.
*G01N 33/24* (2006.01)
*G01F 1/36* (2006.01)
*E21B 47/10* (2012.01)
*F24T 10/20* (2018.01)
*E21B 47/00* (2012.01)
*G01G 17/06* (2006.01)
*G01N 5/00* (2006.01)

(52) U.S. Cl.
CPC ............... *G01F 1/36* (2013.01); *G01G 1/00* (2013.01); *G01G 17/06* (2013.01); *G01N 33/246* (2013.01); *G01N 5/00* (2013.01); *Y02E 10/14* (2013.01)

(56) References Cited

U.S. PATENT DOCUMENTS

2011/0239649 A1 10/2011 Myougan et al.
2017/0276528 A1* 9/2017 Sisler .................... G01N 22/00

* cited by examiner

WEIGHT-BASED PHASE COMPOSITION RATIO DETERMINATION

CROSS REFERENCE TO RELATED APPLICATION(S)

This application is a continuation application of International Application No. PCT/US2015/050808, filed Sep. 17, 2015, which claims the benefit of U.S. Provisional Patent Application No. 62/054,782, filed Sep. 24, 2014 both of which are incorporated herein in their entirety by reference.

RELATED FIELD

At least one embodiment of this disclosure relates generally to a geothermal system, and in particular to determining void fraction or dryness fraction in a geothermal system.

BACKGROUND

Supply of energy resources across the globe is becoming scarce. Various alternative energy sources have been explored, including solar, wind, tidal, and geothermal. Because all of these alternative sources may be unpredictable, various systems have been implemented to accurately and consistently estimate and model the energy output and characteristics of these sources.

Geothermal energy is thermal energy generated and stored in the Earth. From hot springs or other thermal vents, geothermal energy can be extracted and converted into electrical energy. For geothermal, the measurement of void fraction from each vent/spring enables the operators of geothermal wells to calculate the total enthalpy of the two-phase fluids produced from the well, and hence, estimate the energy output. Void fraction or porosity is a measure of the void (i.e., "empty") spaces in a material, and a fraction of the volume of voids over the total volume. For example, the void fraction can be expressed as between 0 and 1 or as a percentage between 0 and 100%. A pump can extract both steam and water (e.g., brine) out of a geothermal vent, creating a gas-liquid two-phase flow. The void fraction can be defined as the fraction of the flow channel volume that is occupied by the gas phase (e.g., steam) or, alternatively, as the fraction of the cross-sectional area of the channel that is occupied by the gas phase.

Conventional techniques of measuring void fraction mostly involve taking the geothermal system out of commission temporarily. For example, a conventional method involves redirecting the output flow from a geothermal well into a separator/silencer assembly to measure the ratio of steam flow and water flow. For another example, the output flow may be redirected into a pressure-controlled pipe to estimate the void fraction. These techniques are disruptive to the energy production cycle of a geothermal power plant.

Recent developments led to a technique of measuring the void fraction via precise metered injection of liquid and vapor phase tracers into the two-phase production pipeline and sampling each phase downstream of the injection point. While this technique does not disrupt the production pipeline, this technique does require additional lab work and does not provide instantaneous feedback of the geothermal well's performance

DISCLOSURE OVERVIEW

Some embodiments disclose techniques for estimating void fractions or dryness fractions in real-time or substantially real-time without disrupting the production flow of the geothermal power plant. Some embodiments describe methods and systems of determining void fraction of a two-phase mixture extracted from a geothermal well or other sources by measuring the fluctuations in weight of transportation units (e.g., pipes) conveying the two-phase mixture. The two-phase mixture includes two or more materials and/or phases (e.g., gas phase, liquid phase, or solid phase) that do not travel together. The two-phase mixture can be a mixture of oil and gas, a mixture of steam and brine, or a mixture of oil and water. For example, a monitor system can utilize one or more load cells external to a transportation unit to measure the fluctuations in the weight of the transportation unit. The load cells can include transducers that are used to convert the change in downward force into weight values. The void fraction changes when the ratio between liquid brine and geothermal vapor (e.g., steam and/or other gases) changes. When the ratio between the liquid brine and the geothermal vapor changes, the weight of the transportation unit also changes. In some embodiments, the load cells are padded with dampeners to prevent damages due to large fluctuations in total weight or slug flow vibrations/oscillations. The weight values can be averaged (e.g., 5 minute intervals) to determine the void fraction of the mixture in real-time.

Although this disclosure discusses computation of a void fraction (e.g., percentage of the volume of gaseous phase material(s) over total volume) in a two-phase mixture, the phase composition monitor 200 can also compute a dryness fraction in a two phase mixture (e.g., percentage of the mass of gaseous phase material(s) over total mass). Because the value of one fraction (e.g., void fraction or dryness fraction) can compute the value of the other, discussions of the estimation of a void fraction of content inside a pipe can equally apply to estimation of the dryness fraction of the content inside the pipe. For example, knowing a slip ratio (e.g., difference or ratio between flow velocity of the gas phase vs. the flow velocity of the liquid phase) of the two-phase mixture can enable the phase composition monitor 200 to compute the void fraction from the dryness fraction and vice versa. Other values derived from the void fraction, such as enthalpy, can also be computed from the dryness fraction. In several embodiments, a void fraction monitor can be referred to a phase composition monitor, which is capable of estimate the void fraction and/or the dryness fraction.

Some embodiments of this disclosure have other aspects, elements, features, and steps in addition to or in place of what is described above. These potential additions and replacements are described throughout the rest of the specification.

The figures depict various embodiments of this disclosure for purposes of illustration only. One skilled in the art will readily recognize from the following discussion that alternative embodiments of the structures and methods illustrated herein may be employed without departing from the principles of the invention described herein.

DETAILED DESCRIPTION

Figure 1:
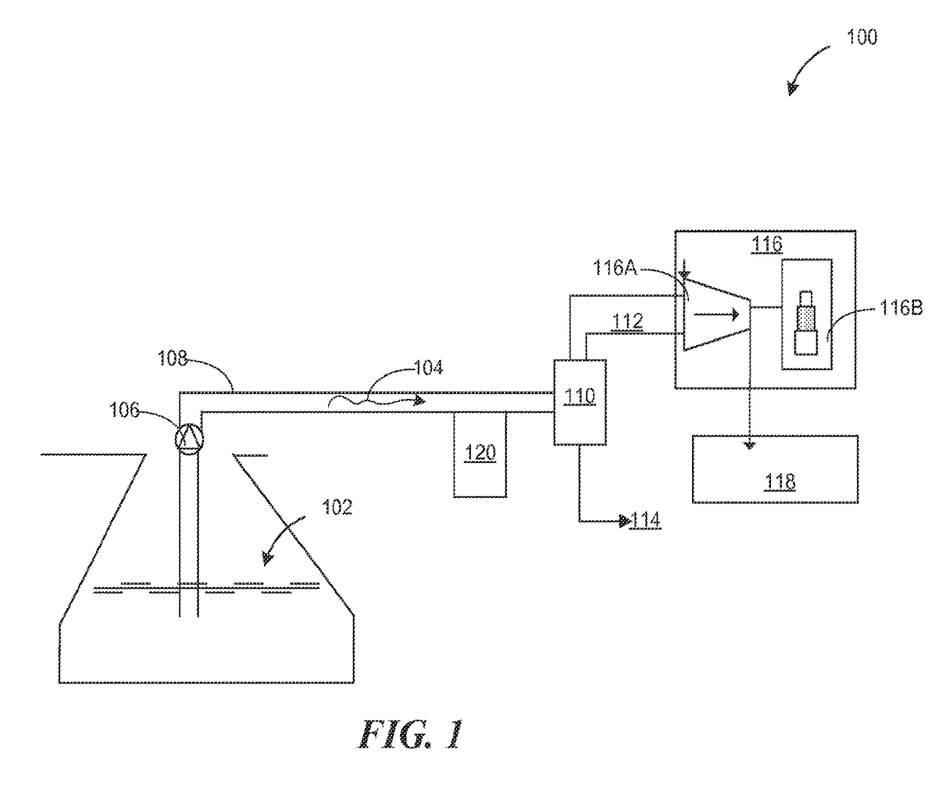
FIG. 1 is a diagram illustrating a geothermal power plant, in accordance with various embodiments.

FIG. 1 illustrates a geothermal power plant 100, in accordance with various embodiments. The geothermal power plant 100 comprises a geothermal well 102 producing a two-phase mixture 104 of saturated steam and hot brine taken via an extraction unit 106. The two-phase mixture 104 is then transported via a transportation unit 108 (e.g., a pipe) to a separator 110. The separator 110 separates geothermal vapor 112 (e.g., the saturated steam and non-condensable gases) from geothermal liquid 114. The separator 110 then supplies the geothermal vapor 112 to a generator unit 116.

The generator unit 116, for example, can be a turbogenerator including a turbine 116A driving an electric generator 116B. The generator unit 116 extracts heat from the steam and produces power, such as electrical power. In some embodiments, the heat-depleted steam exhausted from the generator unit 116 is condensed via a condenser 118 that is supplied with cooling water or other coolant. Water vapor and other non-condensable gases are vented to the atmosphere and hot brine produced from the separator 110 is collected and conveyed back to the geothermal well or to a storage area.

In various embodiments, the geothermal power plant 100 also includes a phase composition monitor 120. The phase composition monitor 120 can determine a real-time or substantially real-time void fraction of the two-phase mixture 104 in the transportation unit 108 based on measuring the fluctuations in weight of the transportation unit 108. In some embodiments, the phase composition monitor 120 is implemented with one or more load cells and a computer system to compute the void fraction. A load cell, for example, can include a transducer that is used to create an electrical signal whose magnitude is directly proportional to the force being measured.

Figure 2:
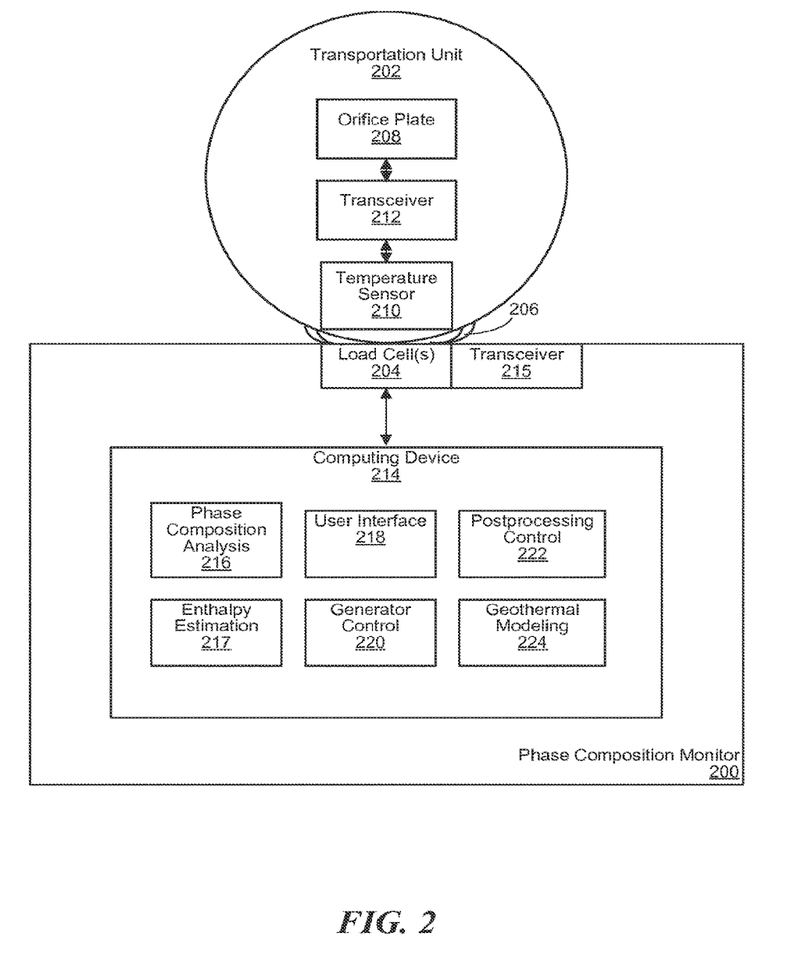
FIG. 2 is a block diagram illustrating a phase composition monitor, in accordance with various embodiments.

FIG. 2 is a block diagram illustrating a phase composition monitor 200, in accordance with various embodiments. The phase composition monitor 200, for example, can be the phase composition monitor 120 of FIG. 1. The phase composition monitor 200 can be coupled to a transportation unit 202, such as the transportation unit 108 of FIG. 1. The phase composition monitor 200 includes one or more load cells 204. The load cells 204 may be coupled onto the transportation unit 202 via a coupling mechanism 206 (e.g., a support cradle of a support stand). The coupling mechanism 206, for example, can be a fastener. The coupling mechanism 206 can also include a dampening structure to protect the load cells 204 from overstressing or being damaged by vibrations or pressure oscillations (e.g., by slug flow).

In some embodiments, the transportation unit 202 includes an orifice plate 208 therein that measures velocity of flow and/or pressure of the mixture in the transportation unit. In some embodiments, the transportation unit 202 includes a temperature sensor 210 therein that measures the temperature of the mixture. In some embodiments, the transportation unit 202 includes a wireless transceiver 212. The wireless transceiver 212 can transmit the pressure measurement and the temperature measurement to the load cells 204 or to a computing system 214. In some embodiments, the computing system 214 can receive the pressure measurement and estimate a temperature reading of the mixture based on a steam table. In some embodiments, the load cells 204 can be coupled to a wireless transceiver 215 that transmits the weight measurements to the computing system 214. In some embodiments, the computing system 214 can be directly coupled via one or more wires/cables to the orifice plate 208, the temperature sensor 210, the load cells 204, or any combination thereof.

The computing system 214 can compute the void fraction or the dryness fraction using the changes in average weight (or average of changes in weight) as measured by the load cells 204. The computing system 214 can then compute the total heat content (e.g., enthalpy) extracted from the geothermal well through the transportation unit 202 based on the pressure measurement, the temperature measurement, and content phase composition ratio (e.g., a void fraction estimation or a dryness fraction estimation).

The computing system 214 can be implemented by one or more computing devices, such as a single processor or multi-processor computer, a distributed computing cluster, a virtualized operating system hosted by a cloud server farm, etc. The computing system 214 can implement one or more functional modules (e.g., as software component or hardware component in the computing system 214). For example, the computing system 214 can include a phase composition analysis module 216, an enthalpy estimation module 217, a user interface module 218, a generator control module 220, a postprocessing control module 222, and a geothermal modeling module 224.

The phase composition analysis module 216 can receive the weight measurements from the load cells 204. The phase composition analysis module 216 can take the differences between the weight measurements to determine the variations in weight over time. The phase composition analysis module 216 can also normalize out noise patterns in the weight measurements attributed to various phenomenon of a two-phase mixture flow. For example, the phase composition analysis module 216 can estimate the void fraction or the dryness fraction via differences between moving averages or periodic averages of weight measurements. Alternatively, the phase composition analysis module 216 can estimate the void fraction or the dryness fraction via averages of the differences between weight measurements.

The phase composition analysis module 216 can implement "virtual dampeners" that analyzes the chaotic signal being obtained from the load cells 204 and normalize out any static signal to get a clearer estimation of the void fraction or the dryness fraction. When the static signal is discounted, the average weight of the transportation unit and content inside can be monitored to estimate the void fraction or the dryness fraction of the content.

Based on the void fraction estimation, dryness fraction estimation, velocity flow/pressure information, and/or temperature information, the enthalpy estimation module 217 can dynamically compute enthalpy in the content of the transportation unit 202 in real-time. This enthalpy estimation can be presented via the user interface module 218. The user interface module 218 can present information about the geothermal well on a display device, via webpage, via an application programming interface (API), an audio speaker, or any combination thereof.

In some embodiments, the estimated enthalpy can be used to control the generator at the geothermal power plant via the generator control module 220, such as controlling a valve to the turbine coupled to the generator. In some embodiments, the estimated enthalpy and the estimated void fraction can be used to control the postprocessing of the geothermal content (e.g., steam and brine) via the postprocessing control module 222. For example, decreasing enthalpy can indicate breakthrough of injection water or invasion of cooler groundwater. Hence, upon detecting decreasing enthalpy, the postprocessing control module 222 can adjust the balance between various connected geothermal wells. For example, often times more than one geothermal wells are allowed to flow fluid into a single separator. The balancing of the geothermal wells connecting to the same separator is part of a "tune-up" of a steam field. The geothermal wells have to be set (e.g., via valves) to the same pressure, and so the geothermal wells that perform better at the defined pressure may be able to connect together, whereas others have worse performance at the same pressure may be used differently. In some rare instances, the postprocessing control module 222 can Temporarily stop or decrease the injection of water down the geothermal well. For another example, increasing enthalpy can indicate reservoir boiling and the formation of a steam cap. In some cases, enthalpy is essential for the interpretation of geochemical data because it determines the steam fraction at sampling conditions and allows the correction of chemical concentrations back to reservoir conditions The geothermal modeling module 224 can use the sensor data from the temperature sensor 210, the load cells 204, and the orifice plate 208 to determine context information about the heat production from the geothermal well. In some cases, the geothermal modeling module 224 can determine potential failure points in the geothermal power plant. For example, a first pattern of noisy variations in weight measurements may trigger an alert that a valve is chattering and about to fail. For another example, a second pattern of noisy variations in weight measurements may trigger an alert of the occurrence of slug flow.

The geothermal modeling module 224 can alert a user through the user interface module 218 when a slug flow pattern is determined. Slug flow pattern prediction can be achieved by monitoring the flow velocity with the orifice plate 208 and/or estimation of the void fraction or the dryness fraction. The combined information from the orifice plate 208 and the dynamic estimation of void fraction or the dryness fraction enables the geothermal modeling module 224 to detect onset triggers of slug flow and/or cyclical patterns of slug flow. This is advantageous over traditional systems that lack the ability to dynamically estimate void fraction or the dryness fraction during production. These contextual patterns, including slug flow patterns, can be time-stamped and tagged with other metadata (e.g., location, magnitude, frequency, etc.) such that the onset of these patterns (e.g., slug flow) can be compared with other phenomenon being measured around the steam field of the geothermal well or geothermal wells of the same reservoir.

In some embodiments, the geothermal modeling module 224 can be used to model the reservoir underneath the geothermal well by combining data from multiple geothermal wells connecting to the same reservoir. Traditionally, because void fraction cannot be tracked in real-time, modeling of a reservoir is accomplished by building a static reservoir model to balance the extraction of the two-phase mixture from different geothermal wells and re-injection of the water/liquid back to the geothermal wells. In some embodiments, the geothermal modeling module 224 can generate a 3D map of the reservoir based on the locations of the geothermal wells. The 3D map can illustrate a heat map corresponding to the enthalpy computed by the computing system 214 in real-time. With multiple geothermal wells monitored, and all the results aggregated in a 3D spatial model/display, for example, the geothermal modeling module 224 can accurate predict trigger-based and cyclical behaviors of a geothermal well or reservoir. The triggers and cycles of these behaviors can be identified using statistical analysis (e.g., principal component analysis and/or regression), signal analysis (e.g., Fourier transform and/or auto-correlation) and/or machine learning (e.g., Hidden Markov Model or Gaussian Mixture Model).

Weight Reading Normalization

Several embodiments include a phase composition monitor that relies on determining the contents of a pipe by weighing the overall structure. For example, geothermal piping is supported on pipe support stands throughout a steam field and a load cell sensor is placed it at one or more such support stands. Many factors affect the weight reading detected, such as pipe stresses, support at other locations, and properties of the water itself. Accordingly, the weight measurements can be normalized by taking into account these factors, such as pipe geometry and support, internal pipe pressure, and temperature. For example, if a pipe is made of steel, then the pipe would vary slightly in strength with increasing temperature. This decrease in pipe strength can be an advantage for this sensor application, decreasing the amount of support the pipe provides on its own. The important parameter affected by temperature is the elastic modulus. In most steels this will normally be in the range of $2 \times 10^{11}$ N/m$^2$. In another example, the pipe may have a larger effect on pipe strength with the presence of a fixed support on one end. In some embodiments, the effect of pressure is greater as the pipe diameter increases.

In a simple weight model, without taking pipe strength into account, the weight measured at the center would be expected to be one half of the total weight of the structure. In a circumstance where the center support is offset a small amount from center, this simplistic model of weight would still be the same.

Portions of active components (e.g., sensors, computing devices, functional modules, etc.) associated with the phase composition monitor 200 may be implemented in the form of special-purpose circuitry, in the form of one or more appropriately programmed programmable processors, a single board chip, a field programmable gate array, a network capable computing device, a virtual machine, a cloud-based terminal, or any combination thereof. For example, the components described can be implemented as instructions on a tangible storage memory capable of being executed by a processor or other integrated circuit chip. The tangible storage memory may be volatile or non-volatile memory. In some embodiments, the volatile memory may be considered "non-transitory" in the sense that it is not transitory signal. Memory space and storages described in the figures can be implemented with the tangible storage memory as well, including volatile or non-volatile memory.

Each of the components may operate individually and independently of other components. Some or all of the components may be executed on the same host device or on separate devices. The separate devices can be coupled through one or more communication channels (e.g., wireless or wired channel) to coordinate their operations. Some or all of the components may be combined as one component. A single component may be divided into sub-components, each sub-component performing separate method step or method steps of the single component.

In some embodiments, at least some of the components share access to a memory space. For example, one component may access data accessed by or transformed by another component. The components may be considered "coupled" to one another if they share a physical connection or a virtual connection, directly or indirectly, allowing data accessed or modified from one component to be accessed in another component. In some embodiments, at least some of the components can be upgraded or modified remotely (e.g., by reconfiguring executable instructions that implements a portion of the components). The phase composition monitor 200 may include additional, fewer, or different components for various applications.

Figure 3:
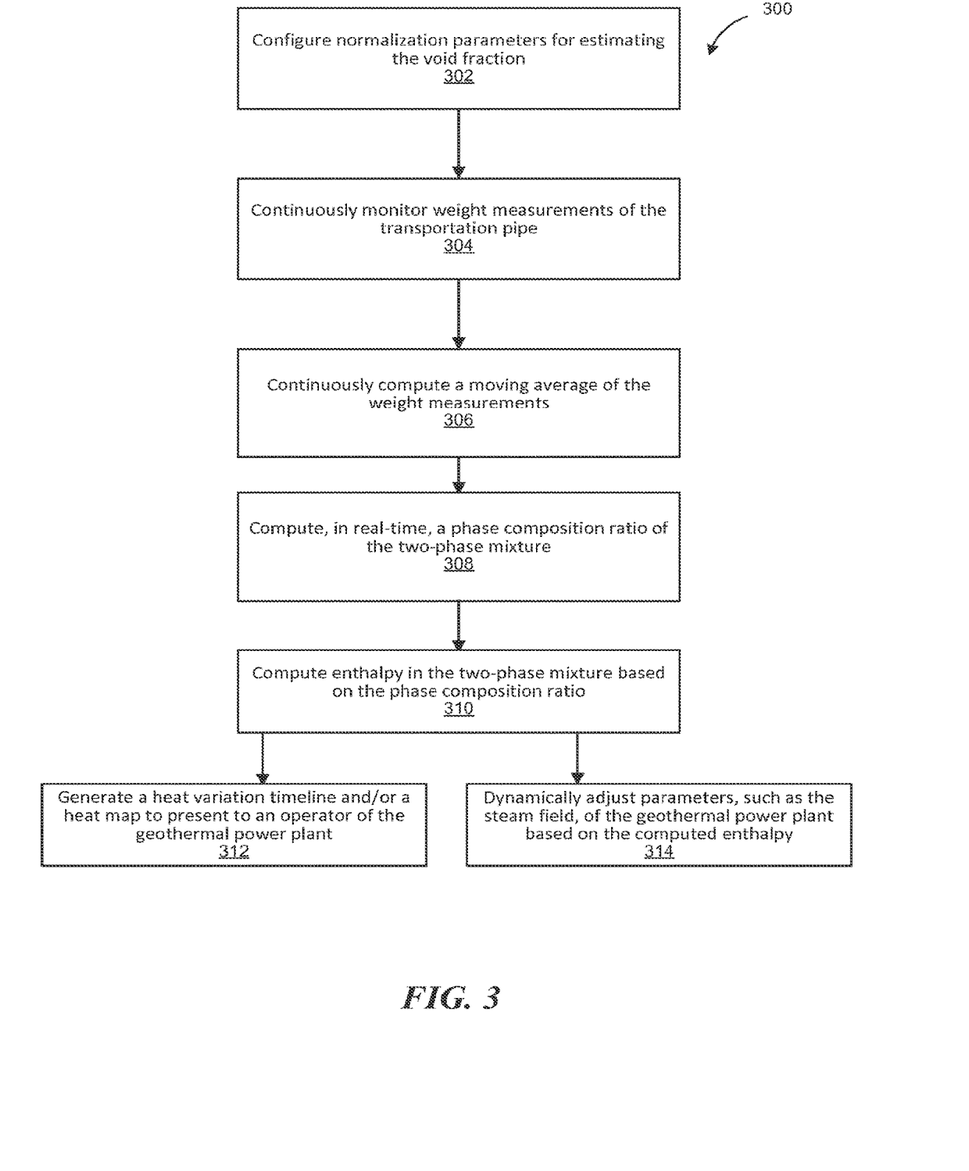
FIG. 3 is a flow chart of a method of operating a phase composition monitor at a geothermal power plant, in accordance with various embodiments.

FIG. 3 is a flow chart of a method 300 of operating a phase composition monitor (e.g., the phase composition monitor 200 of FIG. 2) at a geothermal power plant, in accordance with various embodiments. The method 300 begins at step 302 of configuring normalization parameters for estimating a phase composition ratio. The normalization parameters, for example, can include the estimated or actual weight of a transportation unit (e.g., a pipe), insulation weight of the transportation unit, the weight of a dampener and/or a fastening mechanism, and any other components attached to the transportation unit.

In some embodiments, a computing system (e.g., the computing device 400 of FIG. 4) of the phase composition monitor can present an interface (e.g., a display and keyboard or a touchscreen) for a user to input the normalization parameters. In some embodiments, the normalization parameters can be estimated based on contextual information. For example, the user can input the length and thickness of the transportation pipe, and the computing system can estimate the weight of the transportation pipe based on that information and the expected noise signal from the transportation pipe itself.

At step 304, the computing system can continuously monitor weight measurements of the transportation pipe (e.g., the transportation pipe and its content) from one or more load cells during production operation of a geothermal well. In several embodiments, continuously measuring weight may include measuring weight periodically or according to a non-periodic schedule. The transportation pipe can convey a two-phase mixture extracted from the geothermal well. In order to optimize the steam field to achieve an optimal efficiency, the phase composition monitor has to discern changes in the void fraction of the two-phase mixture within a certain resolution. In some cases, that has been determined to be 2%. This amounts to approximately 0.3% change in the total weight change as observed at the load cells once the weight of the transportation unit is taken into account. Accordingly, the load cells can be selected to have resolution lower than 0.3% of the total weight of the transportation pipe and maximum content therein.

At step 306, the computing system can continuously compute a moving average of the weight measurements. In several embodiments, continuously computing the moving average may include updating the moving average in response to every new weight measurement or every preset number of new weight measurements. At step 308, the computing system can compute, in real-time, a phase composition ratio of the two-phase mixture based on variation of the moving average or variation of the weight measurements. The phase composition ratio can be a void fraction or a dryness fraction. For example, the computing system can compute the change in the dryness fraction directly from the variation of the weight measurements. In turn, the computing system can compute the dryness fraction based on an initial dryness fraction value and the change in the dryness fraction. Optionally, the computing system can compute the void fraction based on the dryness fraction and a slip ratio of the flow velocities between the gas phase and the liquid phase or between two materials. At step 310, the computing system can compute enthalpy in the two-phase mixture based on the phase composition ratio. At step 312, the computing system can generate a heat variation timeline and/or a heat map to present to an operator of the geothermal power plant. At step 314, the computing system can dynamically adjust parameters, such as the steam field, of the geothermal power plant based on the computed enthalpy.

In some embodiments, the computing system can continuously computing a statistical spread measure curve based on the continuously measured weight. The computing system can then detect a slug flow event in the pipe by determining whether the statistical spread measure curve is above a minimum standard deviation level. For example, the statistical spread measure curve is a standard deviation curve or a variance curve.

In some embodiments, the weight measurements is a first weight at a first portion of a pipe system including the pipe. Another load cell can measure continuously a second weight at a second portion of the pipe system downstream from the pipe. The computing system can then compute a flow speed of the two-phase mixture by comparing patterns of the first weight and the second weight within consecutive time windows.

In some embodiments, a temperature sensor in the pipe measures a temperature reading within or at the pipe. In some embodiments, a pressure sensor in the pipe measures a pressure reading within the pipe. The computer system can compute a pipe stress adjustment based on variation in the temperature reading and/or the pressure reading. The computer system can normalize the weight measurements against the pipe stress adjustment.

In some embodiments, the computation of the phase composition ratio and/or the enthalpy are not performed by the phase composition monitor. Rather, the phase composition monitor captures the weight readings and store the weight readings in a data file to be used for post-processing at a later date at an external computer. The external computer can asynchronously generate a 'report' of findings of geothermal well performance for a steam field operator at a later time.

While processes or methods are presented in a given order, alternative embodiments may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. In addition, while processes or blocks are at times shown as being performed in series, these processes or blocks may instead be performed in parallel, or may be performed at different times.

Figure 4:
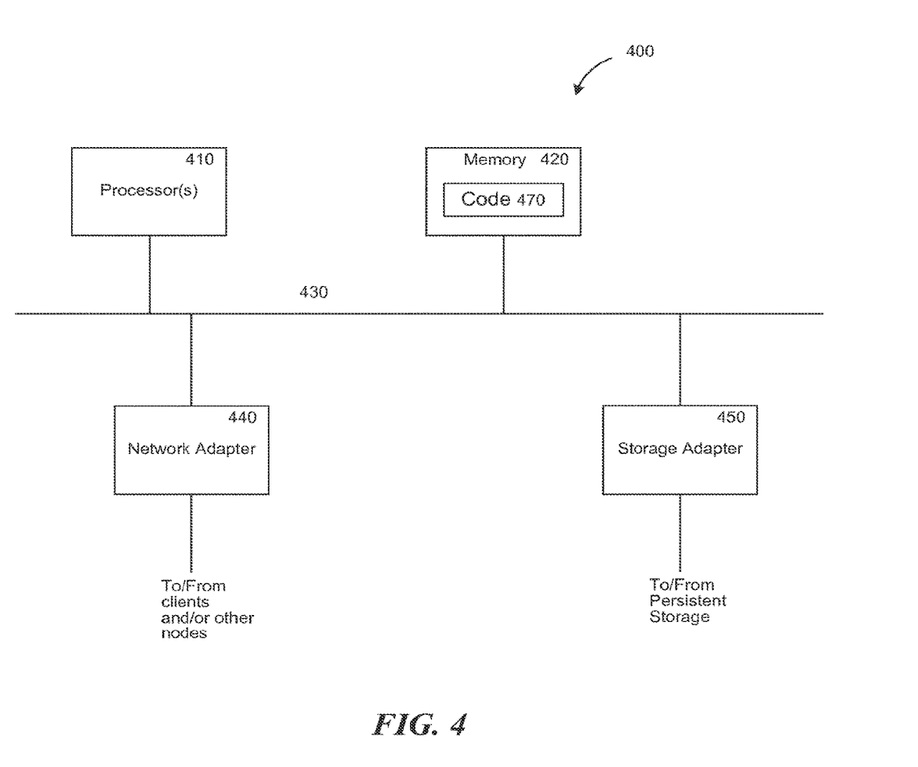
FIG. 4 is a block diagram of an example of a computing device, which may represent one or more computing device or server described herein, in accordance with various embodiments.

FIG. 4 is a block diagram of an example of a computing device 400, which may represent one or more computing device or server described herein, in accordance with various embodiments. The computing device 400 can be one or more computing devices that implement the phase composition monitor 200 of FIG. 2 or methods and processes described in this disclosure. The computing device 400 includes one or more processors 410 and memory 420 coupled to an interconnect 430. The interconnect 430 shown in FIG. 4 is an abstraction that represents any one or more separate physical buses, point-to-point connections, or both connected by appropriate bridges, adapters, or controllers. The interconnect 430, therefore, may include, for example, a system bus, a Peripheral Component Interconnect (PCI) bus or PCI-Express bus, a HyperTransport or industry standard architecture (ISA) bus, a small computer system interface (SCSI) bus, a universal serial bus (USB), IIC (I2C) bus, or an Institute of Electrical and Electronics Engineers (IEEE) standard 1494 bus, also called "Firewire".

The processor(s) 410 is/are the central processing unit (CPU) of the computing device 400 and thus controls the overall operation of the computing device 400. In certain embodiments, the processor(s) 410 accomplishes this by executing software or firmware stored in memory 420. The processor(s) 410 may be, or may include, one or more programmable general-purpose or special-purpose microprocessors, digital signal processors (DSPs), programmable controllers, application specific integrated circuits (ASICs), programmable logic devices (PLDs), trusted platform modules (TPMs), or the like, or a combination of such devices.

The memory 420 is or includes the main memory of the computing device 400. The memory 420 represents any form of random access memory (RAM), read-only memory (ROM), flash memory, or the like, or a combination of such devices. In use, the memory 420 may contain a code 470 containing instructions according to the system disclosed herein.

Also connected to the processor(s) 410 through the interconnect 430 are a network adapter 440 and a storage adapter 450. The network adapter 440 provides the computing device 400 with the ability to communicate with remote devices, over a network and may be, for example, an Ethernet adapter or Fibre Channel adapter. The network adapter 440 may also provide the computing device 400 with the ability to communicate with other computers. The storage adapter 450 enables the computing device 400 to access a persistent storage, and may be, for example, a Fibre Channel adapter or SCSI adapter.

The code 470 stored in memory 420 may be implemented as software and/or firmware to program the processor(s) 410 to carry out actions described above. In certain embodiments, such software or firmware may be initially provided to the computing device 400 by downloading it from a remote system through the computing device 400 (e.g., via network adapter 440).

The techniques introduced herein can be implemented by, for example, programmable circuitry (e.g., one or more microprocessors) programmed with software and/or firmware, or entirely in special-purpose hardwired circuitry, or in a combination of such forms. Special-purpose hardwired circuitry may be in the form of, for example, one or more application-specific integrated circuits (ASICs), programmable logic devices (PLDs), field-programmable gate arrays (FPGAs), etc.

Software or firmware for use in implementing the techniques introduced here may be stored on a machine-readable storage medium and may be executed by one or more general-purpose or special-purpose programmable microprocessors. A "machine-readable storage medium," as the term is used herein, includes any mechanism that can store information in a form accessible by a machine (a machine may be, for example, a computer, network device, cellular phone, personal digital assistant (PDA), manufacturing tool, any device with one or more processors, etc.). For example, a machine-accessible storage medium includes recordable/non-recordable media (e.g., read-only memory (ROM); random access memory (RAM); magnetic disk storage media; optical storage media; flash memory devices; etc.), etc.

The term "logic," as used herein, can include, for example, programmable circuitry programmed with specific software and/or firmware, special-purpose hardwired circuitry, or a combination thereof.

Figure 5A:
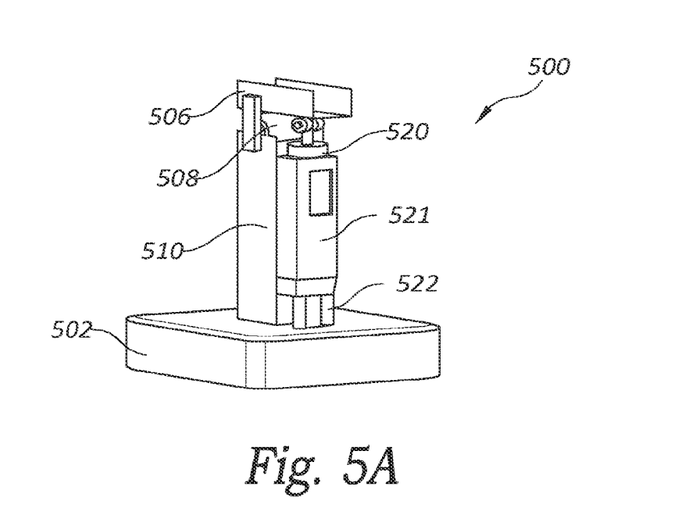
FIG. 5A is a structural diagram illustrating a perspective view of a sliding support of a pipe having a load cell attached thereto, in accordance with various embodiments.

FIG. 5A is a structural diagram illustrating a perspective view of a sliding support 500 of a pipe (e.g., the transportation unit 202) having a load cell 520 attached thereto, in accordance with various embodiments. The sliding support 500 can include a pipe support cradle 506 for engaging with the pipe. The pipe support cradle 506 can be referred to as the "shoe." The pipe support cradle 506 can be a channel of steel or other metal directlyd welded to the pipe. In the illustrated structural diagram, the pipe support cradle 506 rests on (e.g., bears onto) a cylinder 508 on its side. The pipe support cradle 506 can slide on top of the cylinder 508. The cylinder 508 rests on a pillar 510. The pillar 510 rests on a floor base 502 (e.g., concrete base). The cylinder 508 can be welded to the pillar 510 such that the cylinder 508 cannot rotate but supports the pipe support cradle 506 to allow the pipe support cradle 506 to slide as the pipe changes in overall length due to temperature or other factors. The pipe support cradle 506 can be the main item responsible for holding the pipe from significant movement. In some cases, the load cell 520 is under load only by lifting the pipe slightly to clear the pipe support cradle 506.

Figure 5B:
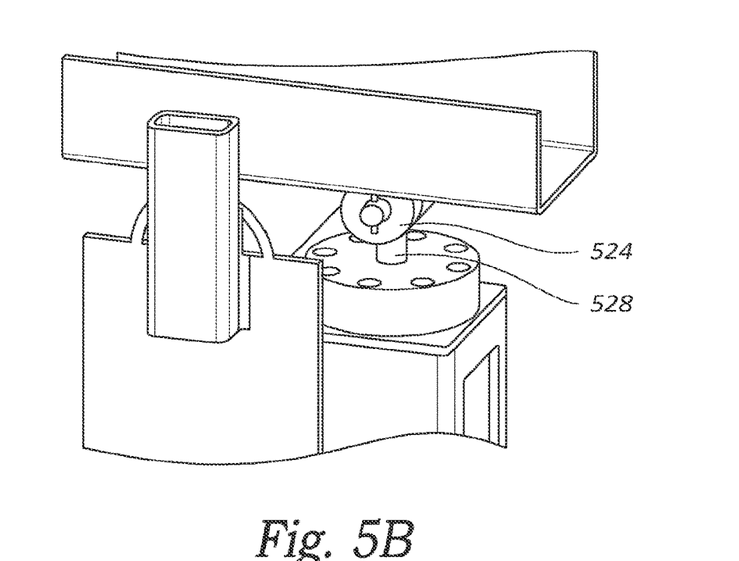
FIG. 5B is the structural diagram of FIG. 5A in a detailed view illustrating a roller and a pivot of the load cell, in accordance with various embodiments.

The load cell 520 rests on a stand structure 521 (e.g., with stand heights from 250 mm to 700 mm). The load cell 520 can be attached to the pillar 510 (e.g., strapped or otherwise fixated). The design of the stand structure 521 can be adjustable (e.g., in length) and capable of removing any sided forces from the load cell 520 itself to allow for accurate readings. To accomplish this, the load cell 520 can include adjustable legs 522 (e.g., adjustable in length and/or angle). The adjustable legs 522 enable the load cell 520 to remain in a vertical position even when the floor base 502 is uneven. The load cell 520 can contact the pipe with a pivoting and rolling contact point to reduce any potential side forces or offset loads. FIG. 5B is the structural diagram of FIG. 5A in a detailed view illustrating a roller 524 and a pivot 528 of the load cell, in accordance with various embodiments. For example, the load cell 520 can include the roller 524 and the pivot 528. In some embodiments, multiple load cells can be locked and stacked together on the adjustable legs 522, allowing for further height adjustment.

Figure 6:
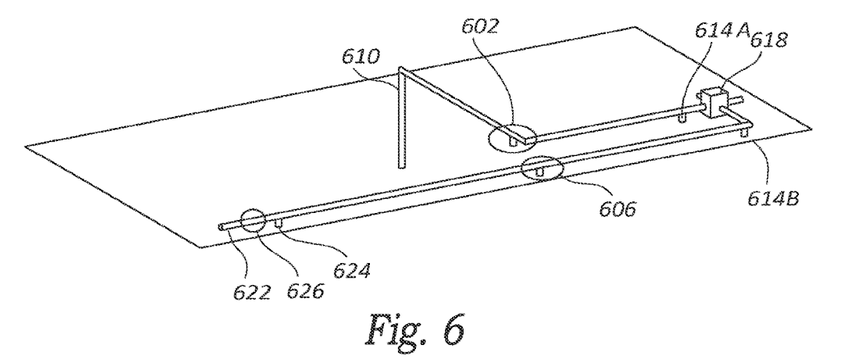
FIG. 6 is an example of a pipe layout diagram of a geothermal power plant, in accordance with various embodiments.

FIG. 6 is an example of a pipe layout diagram of a geothermal power plant 600, in accordance with various embodiments. In this example, the geothermal power plant 600 include two weight sensors (e.g., a weight sensor 602 and a weight sensor 606) mounted respectively to sliding supports (shown as integral to the weight sensors). The weight sensor 602 is closest to a well 610 and located at a position between two fixed supports (e.g., the well 610 itself and a fixed support 614A) near a manifold 618. The weight sensor 606 is located on a sliding support in the piping to a horizontal discharge line 622 as shown between a fixed support 614B and another sliding support 624 without a weight sensor. In normal operation, the well output (e.g., a two-phase mixture) flows through the manifold 618 to a separator (not shown). The well output can be diverted at the manifold 618 into the horizontal discharge line 622 for a well output test. Lip pressure data can be taken at the horizontal discharge line 622. The geothermal power plant 600 can control the wellhead pressure at a throttle valve 626 near the horizontal discharge line 622. The well 610 can run full then throttled in two steps, with sufficient time to allow for stable flow between steps.

Figure 7:
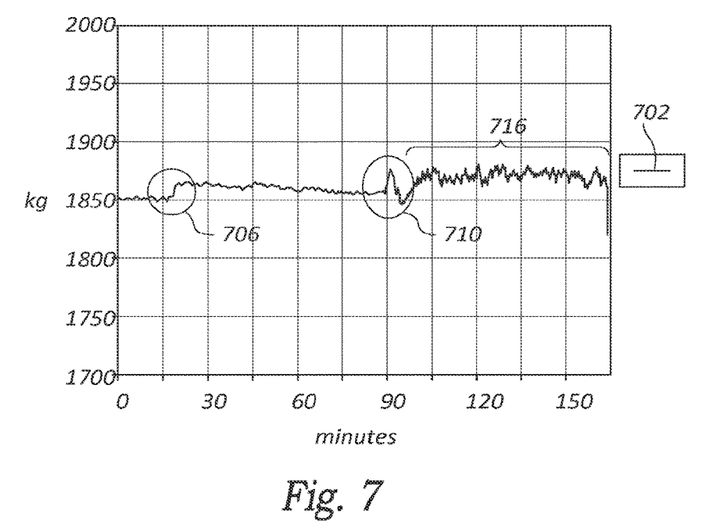
FIG. 7 is an example of a time series graph of weight measurements made by a weight-based phase composition monitor, in accordance with various embodiments.

FIG. 7 is an example of a time series graph of weight measurements 702 made by a weight-based phase composition monitor, in accordance with various embodiments. As shown, the weight measurements 702 fluctuates slightly with occasional larger movements. In some embodiments, the weight-based phase composition monitor only monitors a moving average of the weight measurements 702 to normalize out the slight fluctuations (not shown).

In this example, at a time point 706 the weight measurements 702 experience a weight shift. At a time point 710, the weight measurements 702 experience another weight shift. During time period 716, a spread measurement (e.g., variance or standard deviation) of the weight measurements increases to a higher than average level. This time period 716 of increased spread measurement can correspond to slug flow in a two-phase mixture in geothermal applications.

Figure 8:
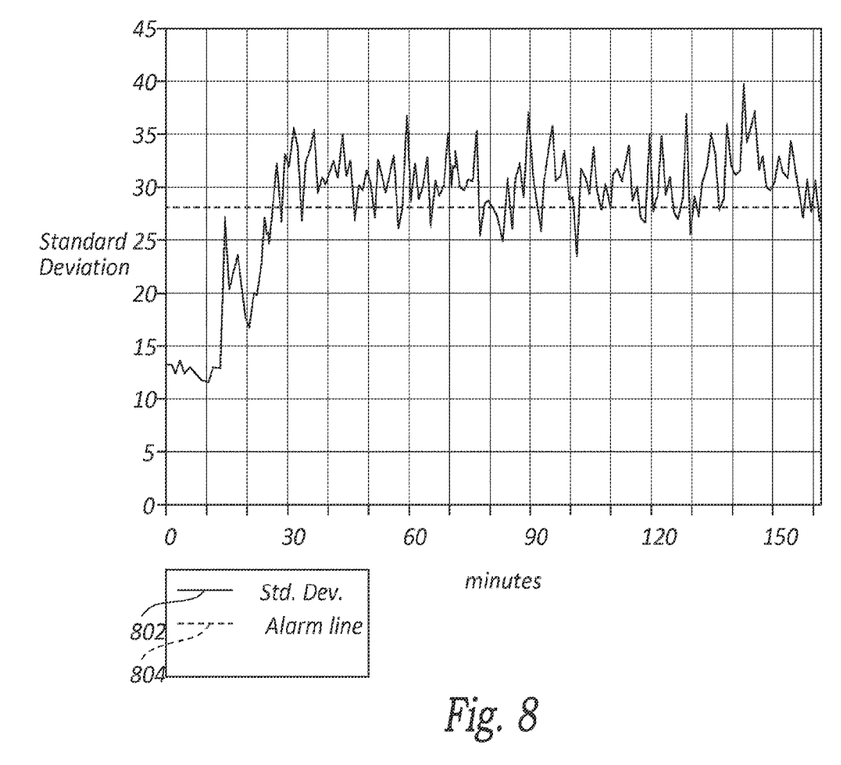
FIG. 8 is an example of a time series graph of moving standard deviations of weight measurements made by a weight-based phase composition monitor, in accordance with various embodiments.

FIG. 8 is an example of a time series graph of moving standard deviations of weight measurements 802 made by a weight-based phase composition monitor, in accordance with various embodiments. In several embodiments, the weight-based phase composition monitor can monitor the standard deviation of the weight measurements 802 in real-time. When the standard deviation increases above an alarm line level 804, the weight-based phase composition monitor can alert the geothermal power plant of the occurrence of slug flow.

Calculation of Enthalpy and Dryness Fraction from Load Cell Data

In some embodiments, the calculation of enthalpy and dryness fraction from load cell data is complicated by the difficulty in obtaining a form of initial value for weight without detailed knowledge of the weight of structural components. In some embodiments, sensor values of weight cannot be directly converted into value of dryness fraction without knowledge of the weights of the rest of the structure, and hence it may be difficult to determine such weights on structures currently in service. Instead, sensor data can be calibrated by use of data from a horizontal discharge test. For example, the value of dryness fraction from the first data point taken for the horizontal discharge can be set to be the first data point value of dryness fraction for calculation of load cell data. This assumes the value of dryness fraction calculated from the first dataset in each horizontal discharge calculation is the 'true' value, and the measured weight from the load cells at that point will be set to be the actual weight of that percent of water in the pipe. Then calculation of additional points will be based on that chosen dryness fraction.

Calculating Changes in Dryness Fraction from Changes in Percent of Water in the Pipe Dryness fraction (x) is defined as the proportion, by weight, of gaseous phase material in a two-phase mixture. A 1% change in liquid phase weight in a pipe structure measured by a load cell would be equal to a 1% change in dryness fraction. Changes in dryness fraction can be calculated from the change in weight measured by the load cell at a pipe support, for example as shown:

Calculation of delta x for load cell data:

$$x(init) - \left(\frac{\Delta w}{w1 * 100}\right) = x(new) \qquad (Eq. 1)$$

x (init)=initial value of x
$\Delta w$=change in weight (delta weight) seen after valve change
w1=weight of a 1% change in water volume in the measured pipe length
x (new)=new value of x Using this technique, and setting x (init) equal to the initial value of x calculated from horizontal discharge data, values of x and enthalpy can be calculated from load cell data.

Some embodiments of the disclosure have other aspects, elements, features, and steps in addition to or in place of what is described above. These potential additions and replacements are described throughout the rest of the specification.

What is claimed is:

1. A method comprising
   continuously measuring weight of a pipe and content of the pipe during production operation of a geothermal well, wherein the pipe conveys a two-phase mixture extracted from the geothermal well, and wherein the two-phase mixture has one or more material substances in at least two of solid phase, liquid phase, and gaseous phase;
   continuously computing a moving average of the measured weight; and
   computing, in real-time, a change in a phase composition ratio of the two-phase mixture based on the computed moving average, where in the phase composition ratio is a void fraction or a dryness fraction.

2. The method of claim 1, further comprising estimating the phase composition ratio based on the change in the phase composition ratio and an initial phase composition ratio value.

3. The method of claim 2, further comprising computing enthalpy in the two-phase mixture based on the estimated phase composition ratio.

4. The method of claim 3, further comprising dynamically adjusting a steam field of a geothermal power plant based on the computed enthalpy.

5. The method of claim 1, further comprising:
   continuously computing a statistical spread measure curve based on the continuously measured weight; and
   detecting a slug flow event in the pipe by determining whether the statistical spread measure curve is above a minimum standard deviation level.

6. The method of claim 5, wherein the statistical spread measure curve is a standard deviation curve or a variance curve.

7. The method of claim 5, further comprising:
   sending an alert message upon the detecting of the slug flow event.

8. The method of claim 1, wherein the weight of the pipe is a first weight at a first portion of a pipe system including the pipe; and the method further comprises:
   measuring continuously a second weight at a second portion of the pipe system downstream from the pipe; and computing a flow speed of the two-phase mixture by comparing patterns of the first weight and the second weight within consecutive time windows.

9. The method of claim 1, further comprising:
determining a temperature reading within or at the pipe;
computing a pipe stress adjustment based on variation in the temperature reading; and
normalizing the weight against the pipe stress adjustment.

10. The method of claim 1, further comprising:
measuring a pressure reading within the pipe;
computing a pipe stress adjustment based on variation in the pressure reading; and
normalizing the weight against the pipe stress adjustment.

11. The method of claim 1, further comprising:
continuously monitoring flow velocity of the content of the pipe; and
detecting an indication of an onset of slug flow or a cyclical pattern of slug flow based on data related to the flow velocity and data related to the void fraction or the dryness fraction.

12. The method of claim 11, further comprising:
time-stamping or tagging data associated with the indication of the onset of slug flow or the cyclical pattern of slug flow.

13. A phase composition monitor comprising
a load cell adapted to couple with a support stand of a pipe and to take weight measurements of the pipe and a two-phase mixture content transported by the pipe;
a transceiver configured to transmit the weight measurements to a computing system; and
the computing system configured to compute a change in a quantitative ratio between two phases or two materials of the two-phase mixture content based on variation of the weight measurements, wherein the quantitative ratio is based on mass or on volume.

14. The phase composition monitor of claim 13, wherein the transceiver is a wireless transceiver.

15. The phase composition monitor of claim 13, wherein the computing system is configured to compute, in real-time, an absolute quantitative ratio based on the computed change in the quantitative ratio and an initial value of the quantitative ratio.

16. The phase composition monitor of claim 13, wherein the load cell is configured to interface with a pipe support cradle of the support stand.

17. The phase composition monitor of claim 16, wherein the load cell includes a roller adapted to interface with the pipe support cradle.

18. The phase composition monitor of claim 17, wherein the roller is adapted with a pivot mechanism.

19. The phase composition monitor of claim 13, wherein the load cell is adapted to be fastened, strapped, and/or attached to the support stand.

20. The phase composition monitor of claim 13, further comprising one or more adjustable length legs that supports the load cell.

21. The phase composition monitor of claim 13, wherein the load cell is a first load cell and the weight measurements are a first set of weight measurements; and the phase composition monitor further comprises a second load cell adapted to take second set of weight measurements at a portion of the pipe different from where the first load cell is taking the first set of weight measurements.

22. The phase composition monitor of claim 21, wherein the computing system is configured to compute a flow speed of the two-phase mixture by comparing patterns of the first set and the second set within consecutive time windows.

23. The phase composition monitor of claim 13, wherein the computing system is configured to compute a statistical spread measure curve based on the weight measurements and to detect a slug flow event in the pipe by determining whether the statistical spread measure curve is above a minimum standard deviation level.

24. The phase composition monitor of claim 23, further including:
an orifice plate adapted to couple with the pipe and to continuously monitor flow velocity of the content of the pipe, wherein the computing system is configured to detect an indication of an onset of the slug flow event based on data related to the flow velocity and data related to the void fraction or the dryness fraction.

25. The phase composition monitor of claim 24, wherein the computing system is configured to time-stamp or tag monitoring data associated with the indication of the onset of the slug flow event to enable a comparison of the monitoring data with other data derived from a phenomenon associated with a geothermal well that is being monitored by the phase composition monitor.

26. The phase composition monitor of claim 13, wherein the computing system is configured to send an alert upon detection of a slug flow event.

27. A geothermal power plant comprising:
a pipe system adapted to convey a two-phase mixture of vapor and brine;
one or more support stands along the length of the pipe system;
one or more load cells coupled to the pipe system to measure changes in weight of one or more sections of the pipe system between pairings of the support stands; and
a computing device configured to compute a quantitative ratio between two phases of the two-phase mixture based on the changes in the weight, wherein the quantitative ratio is based on mass or on volume.

28. The geothermal power plant of claim 27, further comprising: an extraction unit operatively coupled to a geothermal well to extract the two-phase mixture; and wherein the pipe is operatively coupled to the extraction unit.

29. The geothermal power plant of claim 27, further comprising: a generator unit, operatively coupled to the pipe, configured to generate power using the vapor.

30. The geothermal power plant of claim 27, wherein the support stands include at least a first support stand, a second support stand, and a third support stand; and wherein at least one of the load cells is physically coupled to the second support stand and upstream from the third support stand and downstream from the first support stand along the pipe system.

31. The geothermal power plant of claim 30, wherein the second support stand is a sliding support stand and at least one of the first support stand and the second support stand is a fixed support stand.

32. The geothermal power plant of claim 27, wherein at least one of the load cells is physically coupled to a sliding support stand amongst the support stands.

33. The geothermal power plant of claim 32, wherein the at least one load cell is strapped to the sliding support stand.

* * * * *